(12) United States Patent
Anastasi et al.

(10) Patent No.: US 10,044,800 B2
(45) Date of Patent: *Aug. 7, 2018

(54) SYNCHRONIZATION SCHEME FOR PHYSICS SIMULATIONS

(71) Applicant: Microsoft Technology Licensing, LLC, Redmond, WA (US)

(72) Inventors: Marco Anastasi, Edinburgh (GB); Maurizio Sciglio, Edinburgh (GB)

(73) Assignee: Microsoft Technology Licensing, LLC, Redmond, WA (US)

( * ) Notice: Subject to any disclaimer, the term of this patent is extended or adjusted under 35 U.S.C. 154(b) by 267 days.

This patent is subject to a terminal disclaimer.

(21) Appl. No.: 14/880,237

(22) Filed: Oct. 11, 2015

(65) Prior Publication Data

US 2017/0104819 A1 Apr. 13, 2017

(51) Int. Cl.
| | |
|---|---|
| *G06F 17/50* | (2006.01) |
| *H04L 29/08* | (2006.01) |
| *H04L 29/06* | (2006.01) |
| *G06G 7/48* | (2006.01) |
| *G06F 19/12* | (2011.01) |
| *G06F 9/455* | (2018.01) |
| *G06F 17/10* | (2006.01) |

(52) U.S. Cl.
CPC .......... *H04L 67/1095* (2013.01); *G06F 9/455* (2013.01); *G06F 17/10* (2013.01); *G06F 17/50* (2013.01); *G06F 17/5009* (2013.01); *G06F 19/12* (2013.01); *G06G 7/48* (2013.01); *H04L 67/42* (2013.01)

(58) Field of Classification Search
CPC ... H04L 67/1095; H04L 67/42; H04L 43/106; G06F 9/455; G06F 17/50; G06F 17/5009; G06F 19/12; G06F 3/04845; G06F 8/20; G06F 17/10; G06G 7/48; A63F 13/00; A63F 13/10; G01N 33/5008

See application file for complete search history.

(56) References Cited

U.S. PATENT DOCUMENTS 5,625,575 A * 4/1997 Goyal ................ G06F 17/5009
703/6
7,860,827 B1 12/2010 Ayyad
8,468,244 B2 6/2013 Redlich et al.
8,678,929 B1 3/2014 Nishimura et al.
(Continued)

OTHER PUBLICATIONS

He, Kevin, "Scaling a Physics Engine to Millions of Players", Published on: Jul. 19, 2012 Available at: http://gamasutra.com/view/feature/173977/scaling_a_physics_engine_to_.php?print=1.
(Continued)

*Primary Examiner* — Le H Luu
(74) *Attorney, Agent, or Firm* — Klarquist Sparkman, LLP

(57) ABSTRACT

A server, which is in communication with a plurality of client computing devices configured to perform a reduced simulation function, comprises a synchronization engine configured to generate synchronization packets for one or more rigid bodies according to a synchronization scheme and, for each rigid body, to dynamically update the synchronization scheme based on a current state of the rigid body in simulation data and stored states for the rigid body which are stored in a buffer. The synchronization packets are then transmitted to one of the plurality of client computing devices.

20 Claims, 9 Drawing Sheets

(56) References Cited

U.S. PATENT DOCUMENTS

| | | | |
|---|---|---|---|
| 8,751,204 B2 | 6/2014 | Falash et al. | |
| 8,832,568 B2 | 9/2014 | Baszucki | |
| 8,840,475 B2 | 9/2014 | Perlman et al. | |
| 9,005,027 B2 | 4/2015 | Lee et al. | |
| 2003/0195735 A1* | 10/2003 | Rosedale | G06F 17/5009 703/13 |
| 2006/0149516 A1* | 7/2006 | Bond | A63F 13/10 703/6 |
| 2008/0021679 A1* | 1/2008 | Bleiweiss | A63F 13/00 703/2 |
| 2010/0153082 A1* | 6/2010 | Newman | G01N 33/5008 703/11 |
| 2011/0246949 A1* | 10/2011 | Baszucki | G06F 3/04845 715/848 |
| 2011/0295563 A1* | 12/2011 | McDaniel | G06F 17/5009 703/1 |
| 2012/0284002 A1* | 11/2012 | McDaniel | G06F 17/5009 703/2 |
| 2014/0274370 A1 | 9/2014 | Shah | |
| 2014/0358505 A1* | 12/2014 | Hashash | G06F 17/5009 703/2 |
| 2015/0227651 A1* | 8/2015 | Gowaikar | G06F 17/5009 703/2 |
| 2016/0293133 A1* | 10/2016 | Dutt | G06F 8/20 |
| 2017/0104661 A1* | 4/2017 | Anastasi | H04L 43/106 |

OTHER PUBLICATIONS

Fiedler, Glenn, "Networked Physics (2004)", Published on: Jan. 30, 2009 Available at: http://gafferongames.com/game-physics/networked-physics/.

Alinone, Alessandro, "Optimizing Multiplayer 3D Game Synchronization Over the Web", Published on: Oct. 7, 2013 Available at: http://blog.lightstreamer.com/2013/10/optimizing-multiplayer-3d-game.html.

Fiedler, Glenn, "Gaffer on Games", Published on: Mar. 14, 2015 Available at: http://gafferongames.com/networked-physics/introduction-to-networked-physics/.

Deshpande, et al., "Use of Simulation to Test Client-Server Models", In Proceedings of 28th Conference on Winter Simulation, Nov. 8, 1996, pp. 1210-1217.

Bernier, Yahn W., "Latency Compensating Methods in Client/Server In-game Protocol Design and Optimization" Published on: Jun. 18, 2015 Available at: http://www.vis.uni-stuttgart.de/plain/seminare/computerspiele/latency.pdf.

\* cited by examiner

SYNCHRONIZATION SCHEME FOR PHYSICS SIMULATIONS

BACKGROUND

Computer simulation of large-scale physics events, such as the destruction of an entire building or group of buildings, is computationally expensive because of the large number of objects (e.g. individual fragments) involved. In many examples, more objects are required in order to achieve realistic destruction than can be handled on a single compute device and so the destruction which is simulated needs to be approximated or limited in some way.

SUMMARY

The following presents a simplified summary of the disclosure in order to provide a basic understanding to the reader. This summary is not intended to identify key features or essential features of the claimed subject matter nor is it intended to be used to limit the scope of the claimed subject matter. Its sole purpose is to present a selection of concepts disclosed herein in a simplified form as a prelude to the more detailed description that is presented later.

A server, which is in communication with a plurality of client computing devices configured to perform a reduced simulation function, comprises a synchronization engine configured to generate synchronization packets for one or more rigid bodies according to a synchronization scheme and, for each rigid body, to dynamically update the synchronization scheme based on a current state of the rigid body in simulation data and stored states for the rigid body which are stored in a buffer. The synchronization packets are then transmitted to one of the plurality of client computing devices.

Many of the attendant features will be more readily appreciated as the same becomes better understood by reference to the following detailed description considered in connection with the accompanying drawings.

DESCRIPTION OF THE DRAWINGS

The present description will be better understood from the following detailed description read in light of the accompanying drawings, wherein.

Like reference numerals are used to designate like parts in the accompanying drawings.

DETAILED DESCRIPTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

As described above, when simulating a large-scale physics event more objects may be required in order to achieve realistic destruction than can be handled on a single compute device and so the simulation may be performed on a server or group of distributed servers and the results of the simulation may then be communicated to the client computing device. However, the large number of objects involved in the simulation means that there is a large amount of data that needs to be transmitted to the client (e.g. all the data will not fit into a single frame). Where a client has to wait to receive all the transmitted data this may introduce artifacts which impair the user experience. For example, the delay may introduce pauses in the simulation as observed by a user of the client computing device (e.g. a player of a computer game which includes the large-scale physics event) and this significantly impairs the user experience as the simulation appears to stop and start (e.g. it is jerky).

Figure 1:
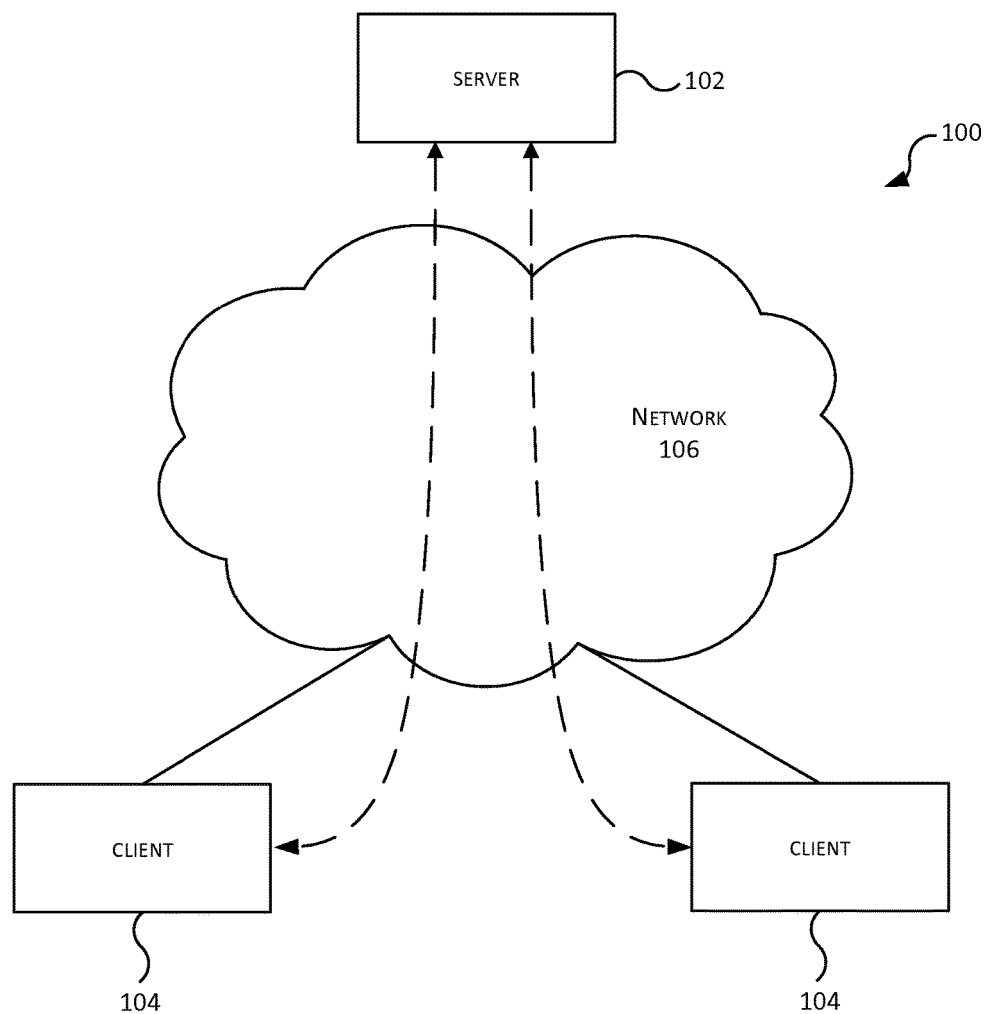
FIG. 1 is a schematic diagram of a system comprising a server connected to one or more client computing devices.

FIG. 1 is a schematic diagram of a system 100 comprising a server 102 connected to one or more client computing devices 104 via a network 106. As described above, if the server 102 performs simulation of a large-scale physics event (such as simulation of a large explosion) then there is a lot of data that needs to be transmitted to the client computing device(s) 104 in order that they can render computer graphics showing the particular event. If the data cannot fit within a single frame (e.g. if more data is produced in a 33 ms frame than can be transmitted in 33 ms) delays are introduced which results in the user experience becoming jerky. Additionally, the available bandwidth for the last mile of the link to each client computing device 104 can vary significantly during a session due to extra network load from other processors (e.g. another user in the same home starting up a video streaming service on a different computing device which shares the same access network, e.g. the same WiFi™ network and the same link from the home to the curbside box).

The embodiments described below are not limited to implementations which solve any or all of the disadvantages of known simulation systems and methods.

Described herein are systems and methods for performing simulation of large-scale physics events (although the systems may also be used for simulation of smaller scale events). The physics simulation is performed on both the server and the client and the physics simulation on the client is kept in synchronization with the simulation on the server (which is the authoritative or master physics simulation). It is not possible just to initiate the physics simulation independently on the server and the client with the same input parameters and then assume that the simulations will proceed identically because physics simulations are not entirely predictable as the simulation involves use of random numbers and furthermore, as described above, the simulation of a large-scale physics event may be too computationally intense to be performed on a single client computing device.

In order to reduce the computational load on the client computing device, a reduced physics simulation is performed on the client by disabling (or otherwise not performing) collision detection. Consequently, the physics engine running on the client computing device simulates the motion of rigid bodies that are not subject to external forces other than gravity (i.e. such that they follow purely ballistic/gravitational trajectories, where the term 'ballistic' encompasses additional forces such as drag, wind, etc. as well as gravity). The server runs a fully authoritative physics simulation and provides synchronization data to the client according to a synchronization scheme. Without this synchronization data, falling bodies would just continue to fall (as there will not be a collision to stop them) and so a user might, for example, see an object fall through the ground or see a ball thrown at a wall pass through the wall. To prevent this happening, the server identifies transitions between a ballistic/gravitational state and a colliding state and modifies the synchronization scheme used.

As described in detail below, the synchronization scheme identifies rigid bodies (where the terms chunk, rigid body and object are used synonymously) which are transitioning between a 'continuously colliding' state in which a body repeatedly collides with other bodies and a 'steady gravitational' state in which no external forces (other than gravity) are applied to the rigid body and changes the synchronization scheme for the rigid body based on these detected transitions. For example, once a body is in the 'steady gravitational' state no synchronization data is provided for that body and the simulation of the body's motion is performed independently on the client device. In order to detect when a rigid body transitions between a 'continuously colliding' state and a 'steady gravitational' state, the state of the rigid body is tracked and a plurality of previous states are stored in a buffer, e.g. N previous states may be stored, where N is a positive integer which is greater than or equal to two.

The simulation of ballistic/gravitational trajectories which is performed on the client device can be performed using limited computation processing resources (i.e. at low CPU expense); however, the use of synchronization enables the full, detailed simulation to be rendered on the client computing device. As a consequence of some of the simulation being performed on the client computing device, the amount of data that needs to be sent to the client device is reduced significantly (e.g. by around 70%).

The method described herein may be referred to as a 'hybrid synchronization model' because the server is authoritative and performs the full physics simulation while the client performs a reduced simulation where collisions between physical bodies are disabled. Under these conditions, unless a physical body is subject to external forces, its position will follow a purely ballistic/gravitational trajectory. Using this hybrid model, the server does not send any synchronization data to clients for bodies that are in the 'steady gravitational' state which results in a significant saving in bandwidth usage. Furthermore, using the techniques described below, the amount of data which is sent relating to bodies which are in the 'continuously colliding' state can be reduced (e.g. based on a parameter K, where K is a positive integer greater than one) and can, in various examples, be varied for different client devices depending upon the available bandwidth between the client and the server (e.g. by having different values of K and/or N for different clients).

The use of a buffer (with N≥2) and the states stored therein to detect the transitions reduces the number of transitions which are detected, for example compared to just detecting a transition based on the current state and the previous state, and the buffer eliminates what might be referred to as 'high frequency noise' where an object is colliding in a first frame, not colliding in the second frame, colliding in a third frame, not colliding in a fourth frame, etc.

As described in detail below, a body does not switch out of the synchronization scheme for 'continuously colliding' bodies until it has been not colliding for a number of successive frames, e.g. N frames (i.e. the current frame and the previous N−1 frames).

Figure 2:
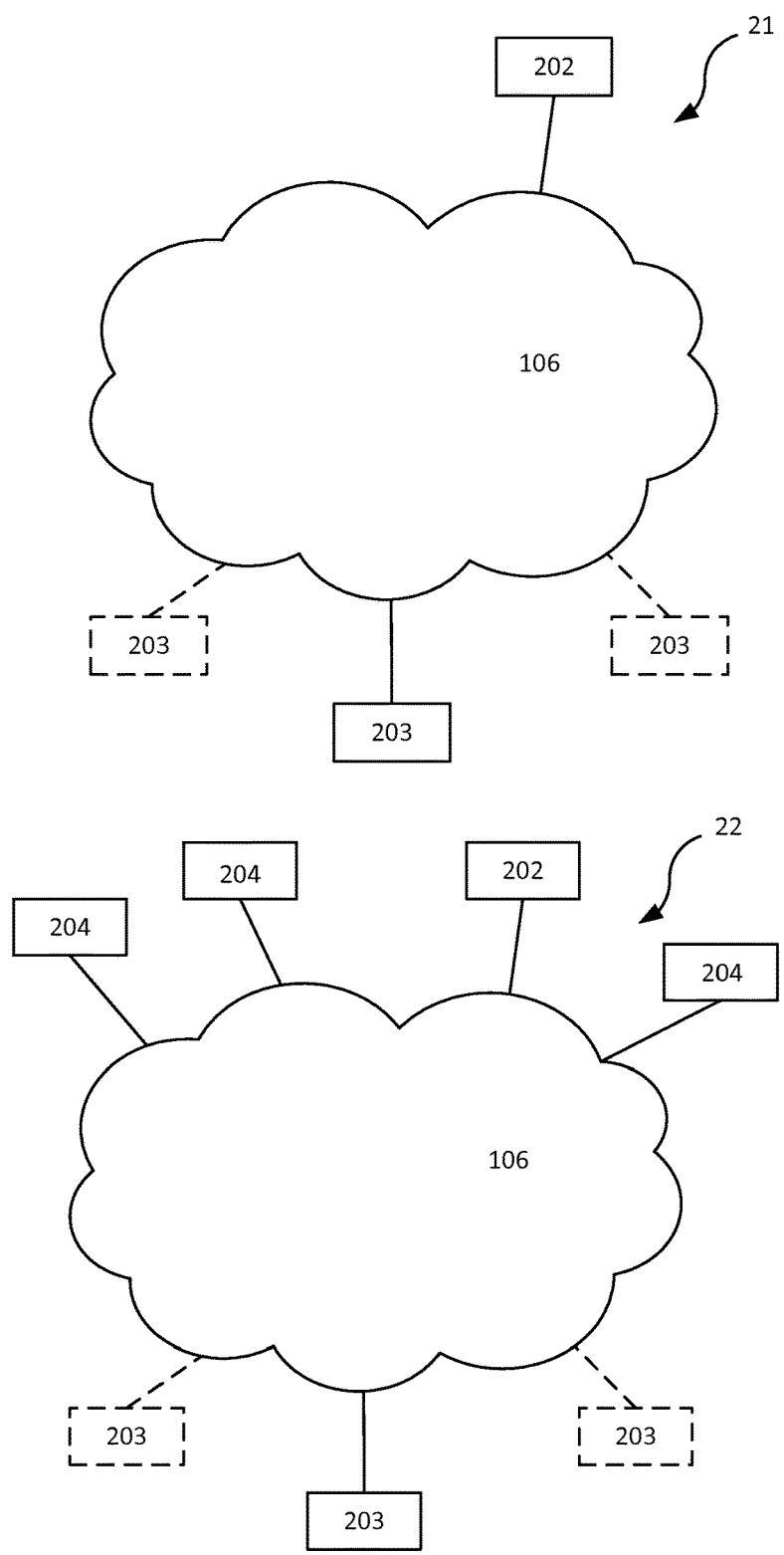
FIG. 2 shows two further example systems.

FIG. 2 shows two example systems 21, 22. The first example system 21 comprises a single server 202 which performs the authoritative physics simulation and one or more client devices 203. As described above, each client device 203 performs physics simulation of ballistic/gravitational trajectories and collision detection is not performed on a client device. A system comprising multiple client devices 203 may be used to render different simulations on different client devices 203 (e.g. where the users of the different clients are playing different computer games) and/or the same simulation on multiple client devices 203 (e.g. where the users are playing the same game). Where multiple users are playing a multi-player game, the methods described herein can be used to keep the simulation synchronized between the server 202 and all the clients 203 which may be important if the users interact in the virtual world and/or are in real-time communication with each other (e.g. via a voice channel) whilst playing the game.

The second example system 22 in FIG. 2 comprises a plurality of servers 202, 204 and one or more client devices 203. Such a system may be used where the physics simulation is distributed across multiple servers 204 (e.g. to increase the computational power available to perform the simulation) and in such an example, a single server 202, which may be referred to as the 'game server', aggregates the results from the simulations performed on each of the physics servers 204 and hence has full visibility of the physics simulation. Again the system may be used to render different simulations on different client devices 203 and/or the same simulation on multiple client devices 203.

Figure 3:
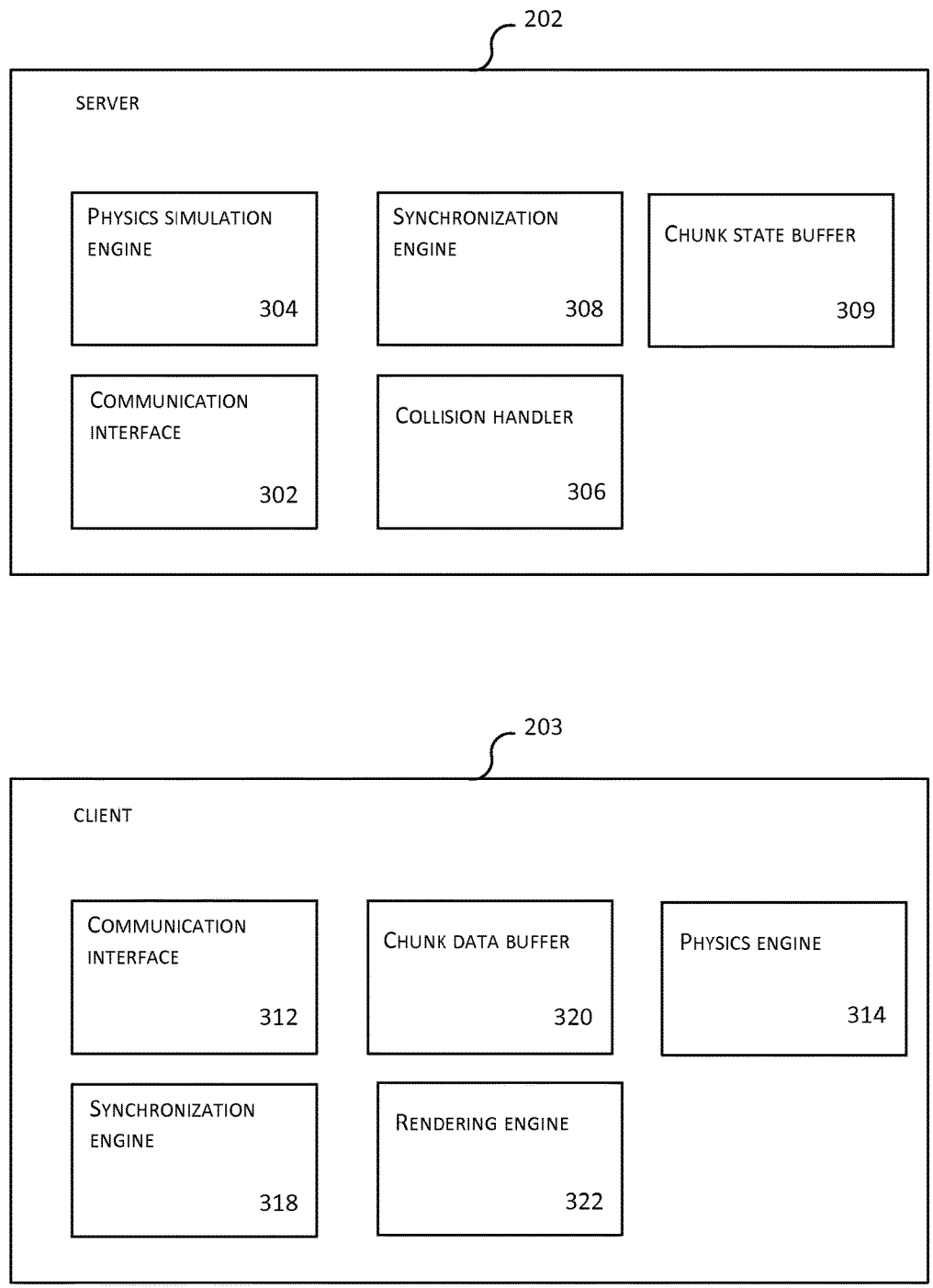
FIG. 3 shows schematic diagrams of an example server and an example client device.

FIG. 3 shows schematic diagrams of a server 202 (e.g. the single server in the system 21 or the game server in the system 22 in FIG. 2) and a client computing device 203.

The server 202 comprises a communication interface 302 via which the server 202 can communicate via the network 106 with other devices, such as other servers 204 and/or client devices 203. The server 202 also comprises a physics simulation engine 304 which has access to data from the full authoritative physics simulation. Depending upon the particular implementation, the physics simulation engine may be configured to perform the full authoritative physics simulation (e.g. as in system 21) or to aggregate simulation results generated by physics engines on one or more other servers 204 (e.g. as in system 22). In some examples, the server 202 may perform some of the full authoritative physics simulation and aggregate the results with simulation results generated by physics engines on one or more other servers 204. Irrespective of whether the physics simulation is performed on the server 202 or on other servers 204, the physics simulation engine 304 has full visibility of the authoritative physics simulation.

The server 202 also comprises a collision handler 306 which is configured to determine on a frame by frame basis whether an object is involved in a collision or not. If an object is determined to have been involved in a collision, the object is flagged and this is referred to herein as the object being marked as 'dirty'. These flags are set and acted upon on a frame by frame basis as described in more detail below. In order to determine if a chunk is dirty, the collision handler 306 is called by the physics simulation engine 304 which provides the full simulation data to the collision handler 306.

The server 202 also comprises a synchronization engine 308 which is configured to provide synchronization packets for transmission to a client device via the communication interface 302. The synchronization engine 308 may also be referred to as a 'chunk distribution manager' as it distributes data about chunks. Each frame the synchronization engine 308 identifies all those chunks that have been marked as dirty and uses a synchronization scheme (described in detail below) to determine on a per-chunk basis, whether data relating to the chunk is to be provided to the client. If the synchronization scheme determines that data relating to a chunk is to be synchronized, the synchronization engine 308 retrieves the properties of the chunk (e.g. linear velocity, angular velocity, position and rotation) and prepares the chunk data to be sent to the client device 203 in synchronization packets, although as described above, depending upon the synchronization scheme, only a proper subset of the properties of a chunk may be included in the chunk data which is sent to the client device. Each data packet may comprise a timestamp to assist the client device 203 in applying the chunk update at the correct time and the timestamp may also be used to detect and address network issues.

The server 202 also comprises a chunk state buffer 309 and this is used by the synchronization engine 308 when implementing the synchronization scheme. The chunk state buffer 309 is arranged to store, for each of a plurality of chunks, the last N states of the chunk (where the state is either dirty or not dirty and in an example, a '1' may represent the dirty state and a '0' may represent the not dirty state). In various examples, the buffer 309 may also store data identifying the last time that the chunk was in the dirty state (e.g. in the example of FIG. 5). The use of this buffer 309 is described in more detail below with reference to FIGS. 4-6.

The client computing device 203 comprises a communication interface 312 via which the client computing device 203 can communicate via the network 106 with other devices, such as the server 202 (and potentially other client devices 203).

The client computing device 203 also comprises a synchronization engine 318 which is configured to insert synchronization packets which have been received from the server 202 via the communication interface 312 into the reduced physics simulation running on the client computing device 203. The synchronization engine 318 may also be referred to as a 'chunk event dispatcher' as it dispatches data about chunks into the local simulation. The synchronization engine 318 uses the timestamps in the received data packets to insert the chunk data into the local simulation at the right time and the local, client, timestamps are synchronized to the server when a client connects to the server and the simulation starts. The timestamps may also be used to identify out-of-order packets which might otherwise corrupt the local simulation.

The local, reduced simulation is performed by the physics engine 314 in the client device 203. As described above, only ballistic/gravitational trajectories are simulated and data on colliding objects is provided by the server 202 in the form of synchronization packets which may also be referred to as 'chunk data'. The chunk data is used to overwrite the transform (e.g. position, rotation and scale) and velocity (both linear and angular) of an object within the simulation. Subsequent simulation of the object is then based on the new transform and velocity.

The client computing device 203 further comprises a rendering engine 322 which is configured to generate a graphical representation of the simulation results (as generated by the physics engine 314) for display to a user.

As shown in FIG. 3, the client computing device 203 may also comprise a buffer 320 in which synchronization packets may be stored between their receipt and their injection into the local simulation under the control of the synchronization engine 318. The use of a buffer 320 provides a level of robustness of the system with respect to network defects (e.g. such that the system can accommodate variations in the time taken for a packet to travel from the server to the client) and the buffer may also be used to amortize the initial spike in data transmission caused by a new triggering event (e.g. a damage event) occurring on the server (and hence a step change in the number of objects for which data is being transmitted from the server to the client).

The operation of the server 202 and its component parts can be described in more detail with reference to FIG. 4, with the method of FIG. 4 being repeated frame by frame.

Following the performance of a step of the physics simulation (block 402), e.g. by the physics simulation engine 304 in the server 202 in system 21 or by a physics engine running on a physics server 204 in system 22 (with the simulation data being received by the physics simulation engine 304 in the server 202 via the communication interface 302), the collision handler 306 identifies the current state ($s_T$) of each of a plurality of chunks (block 404), with the state being either dirty or not dirty. As described above, a chunk has a state of dirty if it was involved in a collision in the frame of the simulation (i.e. in the simulation performed in block 402) and a state of not dirty if it was not involved in a collision in the frame of the simulation.

Once the current state of each chunk has been established by the collision handler 306 (in block 404), the synchronization scheme can be determined for each chunk based on the current state (as determined in block 404) and the tracked state of that chunk (as stored in the chunk state buffer 309) and this is determined by the synchronization engine 308 (blocks 406-416). As described above, the tracked state for a chunk comprises at least the last N states of that chunk.

Figure 4:
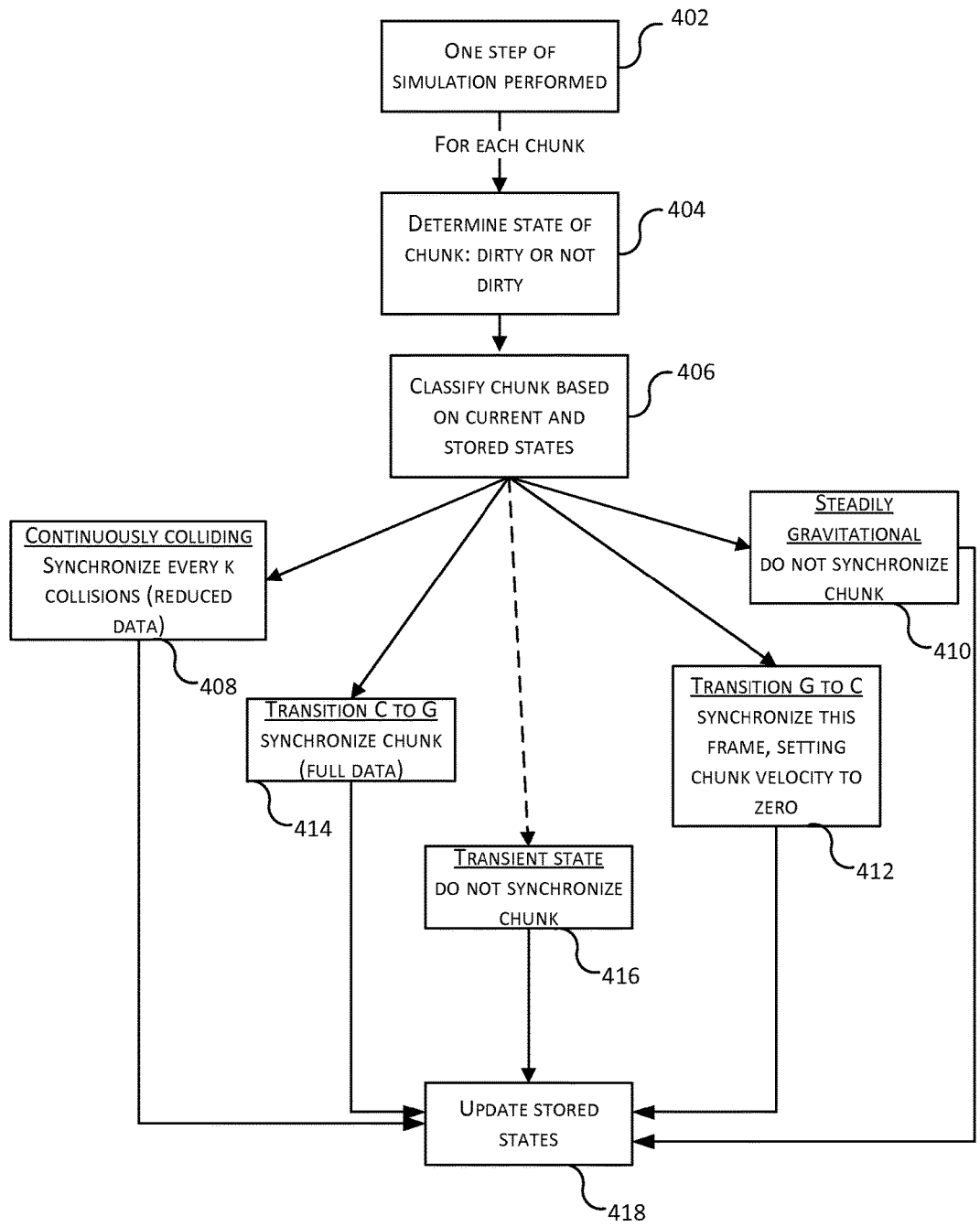
FIG. 4 is a flow diagram of a first example method of operation of the server shown in FIG. 3.

As shown in FIG. 4, the synchronization engine 308 classifies the chunk (in block 406) based on the current and stored states as being: continuously colliding (C), steadily gravitational (G), transitioning from colliding to gravitational (C to G) or transitioning from gravitational to colliding (G to C). A fifth classification may also be used, of the chunk being in a transient or unknown state (T) and this may be used to reduce the number of transitions which are identified in the space of a small number of frames (e.g. C to G to C).

Depending upon the classification (in block 406), the synchronization scheme for the chunk is set as follows:

Continuously colliding (block 408)—data for chunk is sent to the client computing device 203 every K collisions, where K may be fixed or variable and may, in various examples, be set for the client 203 based on the available bandwidth between the server 202 and the client 203. Consequently, the chunk may not be synchronized this frame (e.g. if the last synchronization was less than K frames ago). To further reduce the bandwidth used, reduced chunk data may be provided to the client computing device 203 every K collisions, with this reduced chunk data comprising only transform data (i.e. no velocity data is provided).

Steadily gravitational (block 410)—the chunk is not synchronized (i.e. no data is sent to the client 203).

Transitioning from gravitational to colliding (block 412)—the chunk is synchronized this frame (unlike for the continuously colliding state, where there may be some delay in the synchronization). In this instance, a message is sent to the client 203 (by the synchronization engine 308) to cause the reduced simulation running on the client to stop the chunk straight away (i.e. set its velocity to zero so that it does not move any further in the simulation and remains in the same place until further synchronization data is received from the server).

Transitioning from colliding to gravitational (block 414)—the chunk is synchronized and unlike in the scheme for the continuously colliding state, the entire chunk state is sent to the client 203 (e.g. velocity and transform).

Transient state (block 416)—the chunk is not synchronized (i.e. no data is sent to the client 203).

Having set/adjusted the synchronization scheme for a chunk (in blocks 408-416), the stored states (in buffer 309) are updated (block 418) to include the current state (as determined in block 404) and this results in the eviction of the oldest stored state. The method of FIG. 4 is performed for each chunk and is then repeated for each successive frame in the simulation.

The gravitational to colliding transition and the operation of the corresponding synchronization scheme (in block 412) can be described with reference to an example where the chunk represents a ball which is falling towards the ground. When the ball hits the ground, its state changes to dirty (as determined in block 404, as it has been involved in a collision) and the immediate synchronization setting the velocity of the chunk to zero in the gravitational simulation performed on the client 203 means that the ball stops moving and so does not appear to fall through the ground in the simulation.

The simulation that is then performed on the server 202, 204 (in subsequent frames, block 402) will determine the subsequent motion of the ball (e.g. will it bounce or roll along the ground) and the subsequent state (as determined in block 404 for the chunk for subsequent frames) will determine when further synchronization data is provide to the client 203. In this example, after the frame which identified the transition from gravitational to colliding (block 412), body will be classified as being in the transient state (block 416) for one or more subsequent frames (depending upon the value of N and the precise heuristic used to perform the classification in block 406) before being classified as continuously colliding (block 408) or transitioning from colliding to gravitational (block 414).

Figure 5:
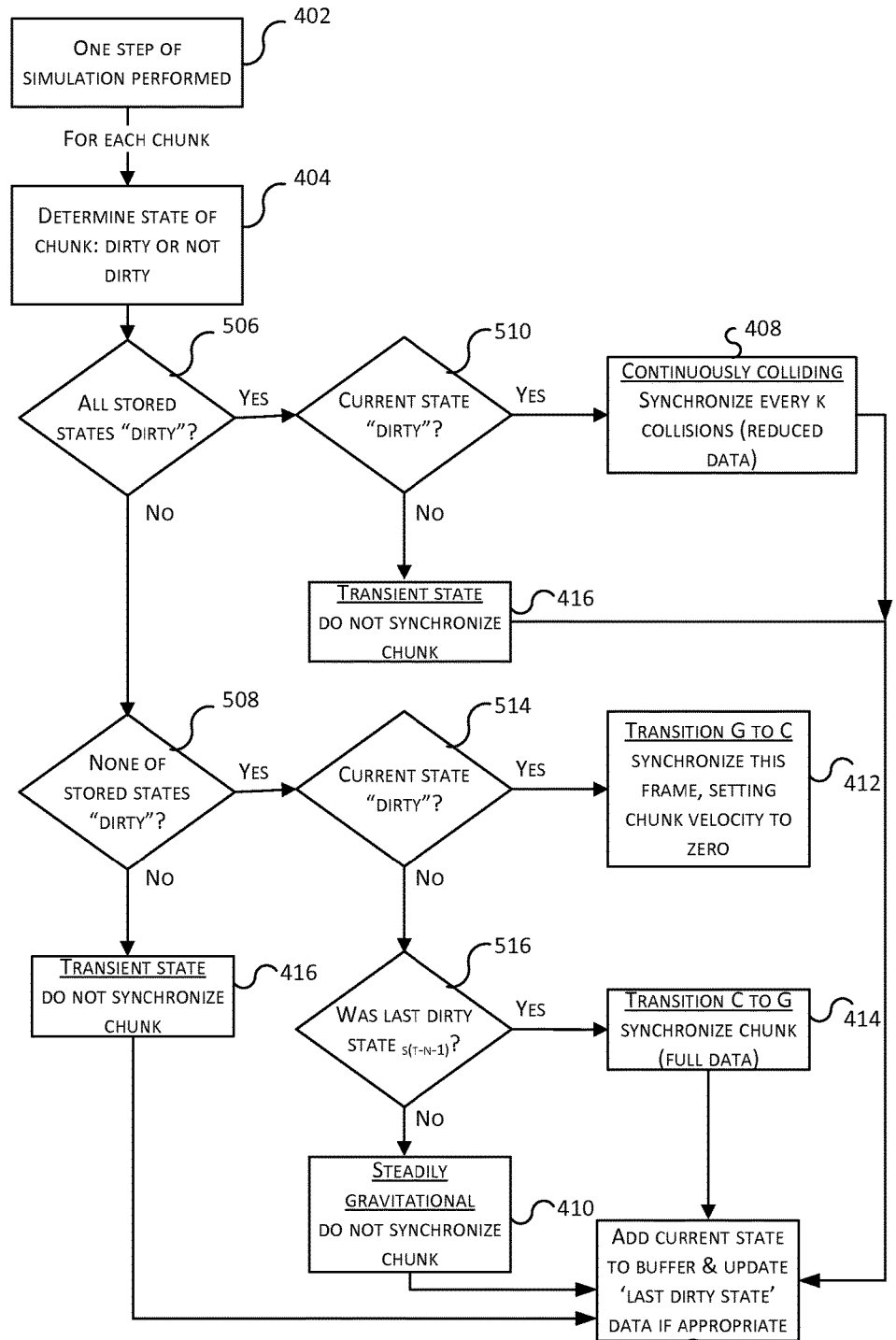
FIG. 5 is a flow diagram of a second example method of operation of the server shown in FIG. 3.

It will be appreciated that there are many different heuristics which may be used in the method of FIG. 4 to classify a chunk based on its current and stored states (in block 406). FIG. 5 shows one example of the heuristics which may be used and for the purpose of the description of FIG. 5 the following notation is used: $s_T$ is the current state of a chunk, $s_{(T-1)}$ is the immediately previous state of the chunk and the buffer 309 stores $s_{(T-1)}, s_{(T-2)}, \ldots, s_{(T-N)}$ along with data identifying when the chunk was last in the dirty state (or at least whether the last state evicted from the buffer was a dirty state).

As shown in FIG. 5, the synchronization scheme for a chunk may be determined by considering whether the stored states (in buffer 309) are all dirty ('Yes' in block 506) or all not dirty ('Yes' in block 508) and although FIG. 5 shows a particular sequence for these questions it will be appreciated that they may be performed in either order or in parallel. If all the stored states are dirty ('Yes' in block 506) and the current state is also dirty ('Yes' in block 510), then the chunk is considered to be in the 'continuously colliding' state and data for chunk is sent to the client computing device 203 every K collisions (block 408).

If none of the stored states are dirty ('Yes' in block 508), the current state is also not dirty ('No' in block 514) and the last dirty state was longer ago than state $s_{(T-N-1)}$ ('No' in block 516), then the chunk is considered to be in the 'steadily gravitational' state and is not synchronized (block 410).

If none of the stored states are dirty ('Yes' in block 508) but the current state is dirty ('Yes' in block 514), then this is considered to be a transition from gravitational to colliding and the chunk is synchronized that frame (block 412).

If however none of the stored states are dirty ('Yes' in block 508), the current state is also not dirty ('No' in block 514) and the last dirty state was in state $s_{(T-N-1)}$ ('Yes' in block 516), then this is considered to be a transition from colliding to gravitational and the chunk is synchronized (block 414), with the entire state being sent to the client as described above.

Figure 7:
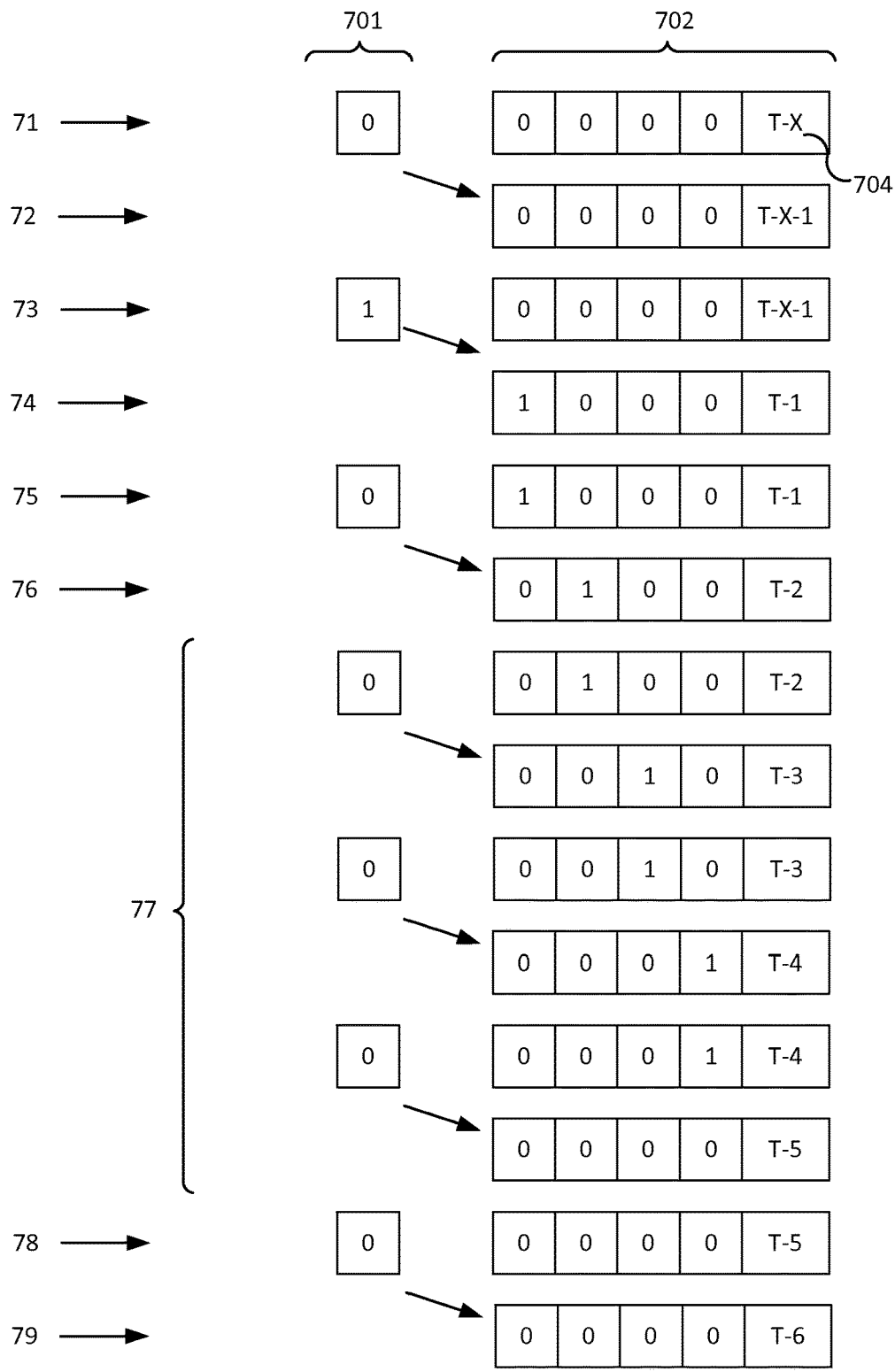
FIG. 7 is a graphical representation of the chunk states in an example using the method of FIG. 5.

Referring back to the ball example described above, the current state 701 and the contents 702 of the buffer 309 when used with the heuristics of FIG. 5 and for N=4 are shown in FIG. 7. If the ball is falling in the current frame, $s_T=0$ (i.e. not dirty) and ball has been falling for more than 5 frames, the N stored states are also all zeros as shown in the first representation 71 in FIG. 7. In this example, the final entry 704 in the buffer 702 shows that the last dirty state was state $s_{(T-X)}$ where X>(N+1). As none of the stored states are dirty ('Yes' in block 508), the current state is not dirty ('No' in block 514) and the last dirty state was not $s_{(T-N-1)}$ ('No' in block 516), the ball is classified as steadily gravitational and the corresponding synchronization scheme is used (block 410). The buffer is then updated as shown in the second representation 72.

The third representation 73 shows the updated buffer (from representation 72) and the current state at the point the ball hits the ground, which is now dirty ($s_T=1$). Following the heuristic of FIG. 5, none of the stored states are dirty ('Yes' in block 508) and the current state is dirty ('Yes' in block 514) and so the ball is classified as transitioning from gravitational to colliding and the corresponding synchronization scheme is used (block 412), which stops the ball from moving further in the simulation performed on the client. The buffer is then updated as shown in the fourth representation 74.

The fifth representation 75 shows the updated buffer (from representation 74) and the current state which in this example assumes that the ball bounces back and so is no longer in collision with the ground and so $s_T=0$ (i.e. not dirty). Following the heuristic of FIG. 5, the stored states are neither all dirty ('No' in block 506) nor all not dirty ('No' in block 508) and so the ball is classified as being in the transient state and the corresponding synchronization scheme is used (block 416), which keeps the ball stationary in the simulation performed on the client. The buffer is then updated as shown in the sixth representation 76.

As shown in the subsequent representations 77 (which follow on the pattern from representations 71-76), the ball remains in the transient state for the next 3 frames. It is not until the following frame, as shown in representation 78 that it changes. In this frame, the ball is still bouncing and so $s_T=0$ (i.e. not dirty). Following the heuristic of FIG. 5, none of the stored states are dirty ('Yes' in block 508), the current state is not dirty ('No' in block 514) and the last dirty state was $s_{(T-N-1)}$ ('Yes' in block 516), the ball is classified as transitioning from colliding to gravitational and the corresponding synchronization scheme is used (block 414) and the client is provided with the full chunk data (including the velocity of the ball) and so its gravitational simulation of the ball can start again. The buffer is then updated as shown in the next representation 79.

Figure 6:
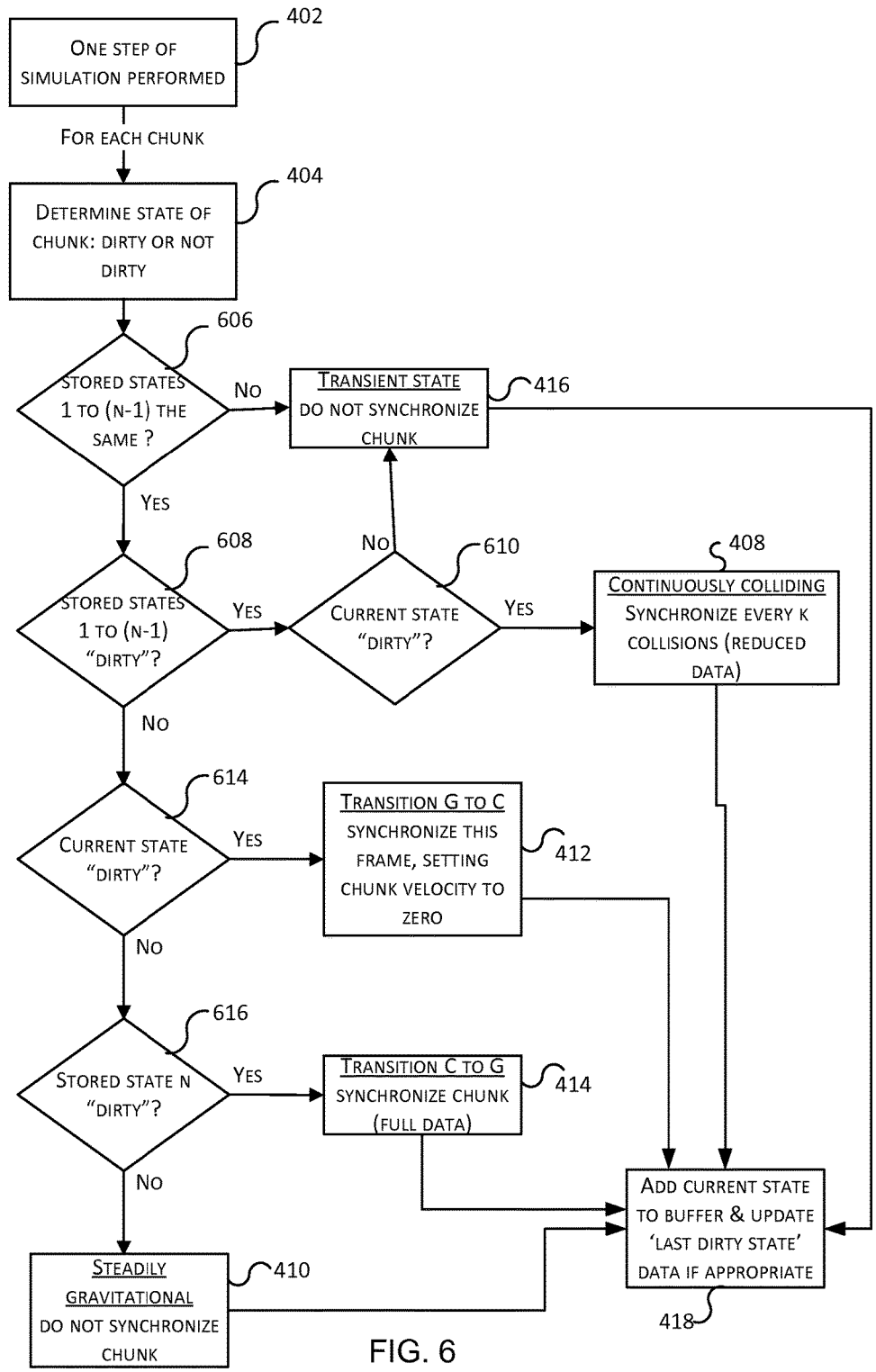
FIG. 6 is a flow diagram of a third example method of operation of the server shown in FIG. 3.

FIG. 6 shows another example of the heuristics which may be used (in block 406) and in this example the buffer 309 stores N states, states 1 to N, with state 1 being the most recently stored state and state N being the oldest stored state and unlike in the example of FIG. 5, the buffer does not store data identifying when the chunk was last in the dirty state or at least whether the last state evicted from the buffer was a dirty state).

As shown in FIG. 6, for each chunk the synchronization scheme for that chunk may be determined by considering whether stored states 1 to (N−1) (in buffer 309) are all the same (block 606) and if so whether they are all dirty or not dirty (block 608). If stored states 1 to (N−1) are not all the same ('No' in block 606), the chunk is considered to be in the transient state and is not synchronized (block 416).

If stored states 1 to (N−1) are all dirty ('Yes' in block 608) and the current state is also dirty ('Yes' in block 610), then the chunk is considered to be in the 'continuously colliding' state and data for chunk is sent to the client computing device 203 every K collisions (block 408).

If stored states 1 to (N−1) are all not dirty ('No' in block 608), the current state is not dirty ('No' in block 614) and stored state N is also not dirty ('No' in block 616), then the chunk is considered to be in the 'steadily gravitational' state and is not synchronized (block 410).

If however, stored states 1 to (N−1) are all not dirty ('No' in block 608), the current state is not dirty ('No' in block 614) but stored state N is dirty ('Yes' in block 616), then this is considered to be a transition from colliding to gravitational and the chunk is synchronized (block 414), with the entire state being sent to the client as described above.

If stored states 1 to (N−1) are all not dirty ('No' in block 608) but the current state is dirty ('Yes' in block 614), then this is considered to be a transition from gravitational to colliding and the chunk is synchronized that frame (block 412).

Figure 8:
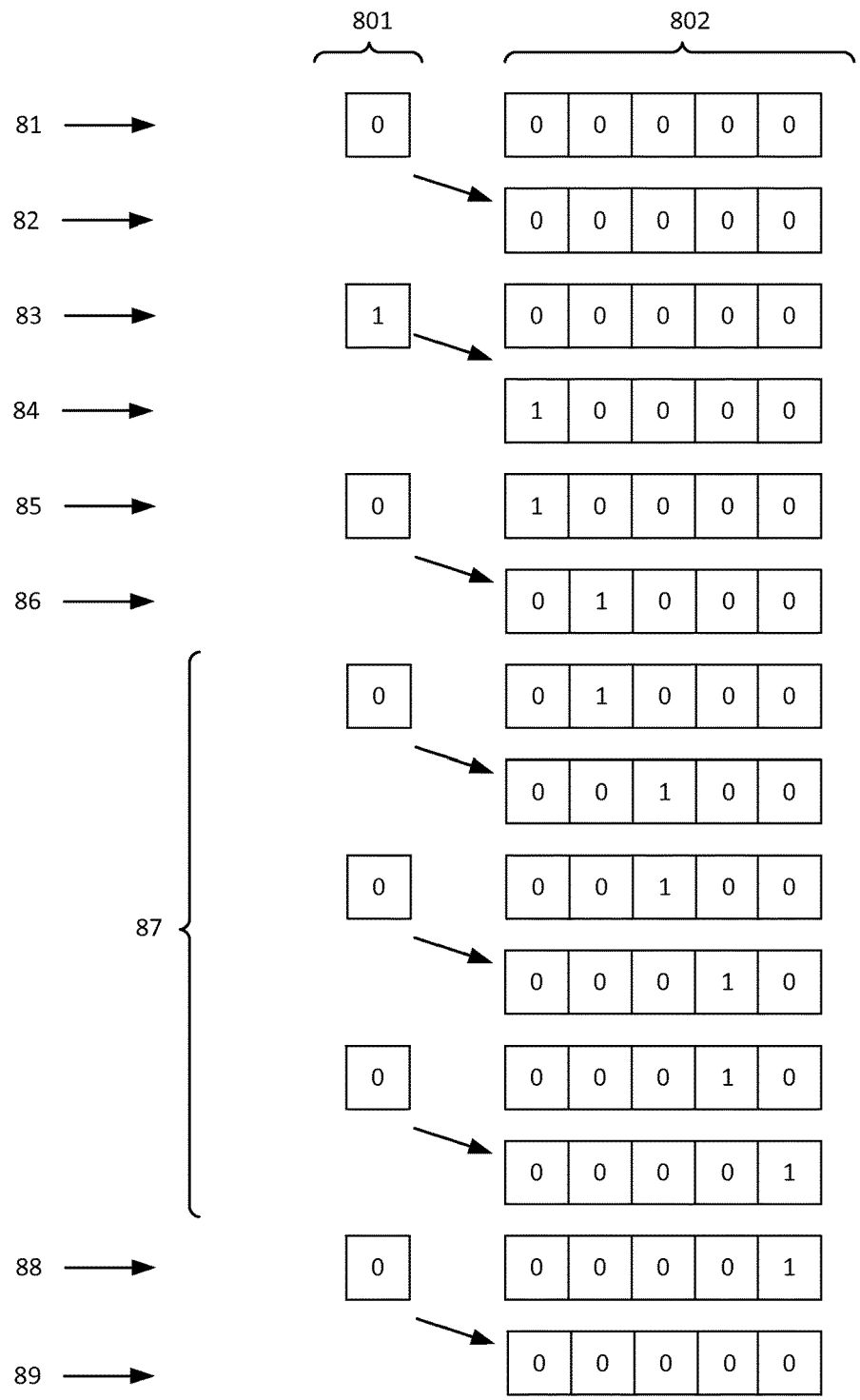
FIG. 8 is a graphical representation of the chunk states in an example using the method of FIG. 6.

Referring back to the ball example described above, the current state 801 and the contents 802 of the buffer 309 when used with the heuristics of FIG. 6 and for N=5 are shown in FIG. 8. If the ball is falling in the current frame, $s_T=0$ (i.e. not dirty) and ball has been falling for more than 5 frames, the N stored states are also all zeros as shown in the first representation 81 in FIG. 8. As none of the stored states 1 to (N−1) are dirty ('Yes' in block 606 and 'No' in block 608), the current state is not dirty ('No' in block 614) and stored state N(=5) is not dirty ('No' in block 616), the ball is classified as steadily gravitational and the corresponding synchronization scheme is used (block 410). The buffer is then updated as shown in the second representation 82.

The third representation 83 shows the updated buffer (from representation 82) and the current state at the point the ball hits the ground, which is now dirty ($s_T=1$). Following the heuristic of FIG. 6, as none of the stored states 1 to (N−1) are dirty ('Yes' in block 606 and 'No' in block 608) and the current state is dirty ('Yes' in block 614), the ball is classified as transitioning from gravitational to colliding and the corresponding synchronization scheme is used (block 412), which stops the ball from moving further in the simulation performed on the client. The buffer is then updated as shown in the fourth representation 84.

The fifth representation 85 shows the updated buffer (from representation 84) and the current state which in this example assumes that the ball bounces back and so is no longer in collision with the ground and so $s_T=0$ (i.e. not dirty). Following the heuristic of FIG. 6, the stored states 1 to (N−1) are not all the same ('No' in block 606) and so the ball is classified as being in the transient state and the corresponding synchronization scheme is used (block 416), which keeps the ball stationary in the simulation performed on the client. The buffer is then updated as shown in the sixth representation 86.

As shown in the subsequent representations 87 (which follow on the pattern from representations 81-86), the ball remains in the transient state for the next 3 frames. It is not until the following frame, as shown in representation 88 that it changes. In this frame, the ball is still bouncing and so $s_T=0$ (i.e. not dirty). Following the heuristic of FIG. 6, none of the stored states 1 to (N−1) are dirty ('Yes' in block 606 and 'No' in block 608), the current state is not dirty ('No' in block 614) and stored state N (=5) is dirty ('Yes' in block 616), so the ball is classified as transitioning from colliding to gravitational and the corresponding synchronization scheme is used (block 414) and the client is provided with the full chunk data (including the velocity of the ball) and so its gravitational simulation of the ball can start again. The buffer is then updated as shown in the next representation 89.

In further example heuristics (which may be different from or variations of those shown in FIGS. 5 and 6) other parameters may additionally, or instead, be used to determine the synchronization scheme. Examples of other parameters which may be used include, but are not limited to, visibility of a chunk from a player's point of view, size of a chunk and how long ago a chunk was last synchronized.

As shown in the examples in FIGS. 7 and 8, the use of the chunk state buffer 309, which stores the previous N states of each chunk, introduces a latency in state transitions (in particular, transitions out of the colliding state). This is particularly visible in the example described and results in the ball appearing "sticky" because whilst in the transient state it does not move and appears stuck to the ground. The latency which is introduced is, in many examples, directly proportional to the value of N and in all examples, increases as N increases. The latency can therefore be reduced by reducing the value of N; however, this does result in an increase in the number of detected transitions (i.e. an increase in occasions when a chunk repeatedly flips between the continuously colliding and steadily gravitational states) and as a result does not reduce the amount of synchronized data as much as for larger values of N. In addition, or instead, particle effects (e.g. smoke or debris) may be applied in the rendering engine (or the physics simulation) running on the client to mask the latency (e.g. effects of dust flying up from the ground so that the "stickiness" of the ball is less obvious or not visible to a user). An alternative is to introduce a server-side delay of N frames, such that physics simulation on the client 203 always runs N frames behind the physics simulation on the server 202, 204. This means that the state $s_T$ on the client can be determined on the server at $s_{(T+N)}$; however, depending upon the delay used, it may be perceptible by a user (e.g. 150 ms is perceptible by some users). Consequently, small values of N (e.g. N=2) can be used but larger values will impair performance (e.g. N=4, which corresponds to a 132 ms delay at 30 fps, will result in a latency that is perceptible to a user as there is additional latency, above the 132 ms, caused by the network connection, input lag, etc.).

Example bandwidth savings that may be achieved using the variable synchronization scheme described herein are around 65% for N=8 and K=4, around 45% for N=4, K=4 and around 40% for N=2, K=4. Best visual results are obtained with N=2 as that introduces the minimum amount of state change latency. Further bandwidth savings can be achieved by increasing the collision replication interval K.

As described above, K and N may be changed dynamically (e.g. by the synchronization engine 308) for each connected client device 203, e.g. based on information which is received at the server 202 and which identifies the available bandwidth between the server and each client (or from which the available bandwidth can be inferred). If low values of N and K are used for a client with a good connection (i.e. with a higher available bandwidth), the user of the client device will have the best visual experience while larger values of N and K will dynamically scale down the visual quality for clients with worse connectivity.

The physics simulation engine 304, collision handler 306 and synchronization engine 308 in the server 202 may be implemented in software or the functionality described may be performed, at least in part, by one or more hardware logic components. For example, and without limitation, illustrative types of hardware logic components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), Graphics Processing Units (GPUs).

Figure 9:
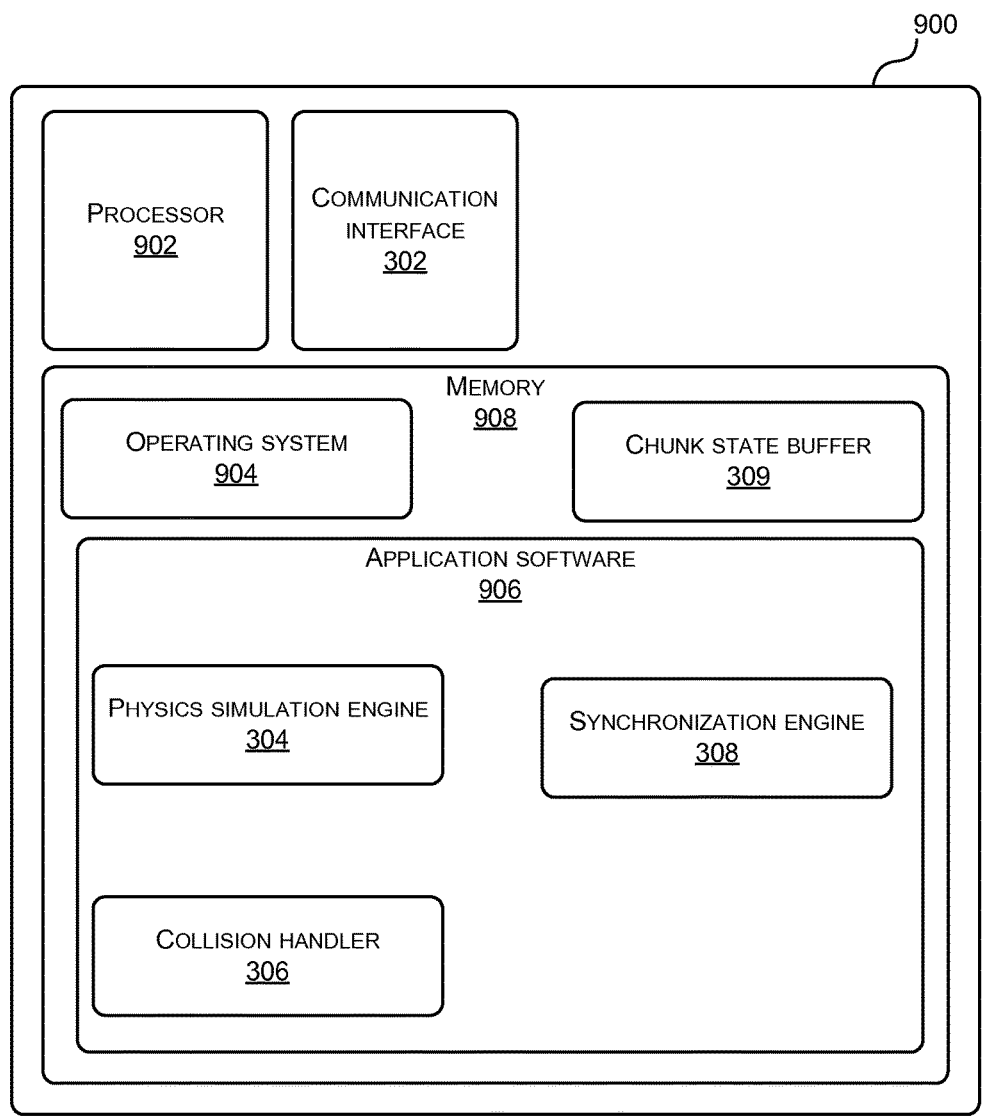
FIG. 9 illustrates an exemplary computing-based device which may perform elements of the method shown in any of FIGS. 4-6.

FIG. 9 illustrates various components of an exemplary computing-based device 900 which may be implemented as any form of a computing and/or electronic device and may operate as a server 202 and in which embodiments of the method of any of FIG. 4-6 may be implemented.

Computing-based device 900 comprises one or more processors 902 which may be microprocessors, controllers or any other suitable type of processors for processing computer executable instructions to control the operation of the device in order to implement the functionality of the server 202. In some examples, for example where a system on a chip architecture is used, the processors 902 may include one or more fixed function blocks (also referred to as accelerators) which implement a part of the method of any of FIGS. 4-6 in hardware (rather than software or firmware).

Platform software comprising an operating system 904 or any other suitable platform software may be provided at the computing-based device to enable application software 906 to be executed on the device. Depending upon the implementation, the application software may include the physics simulation engine 304, synchronization engine 308 and/or collision handler 306.

When implemented in software, the physics simulation engine 304 comprises computer executable instructions which, when executed by the processor 902, cause the processor to perform a physics simulation (e.g. as in block 402) or to receive physics simulation results from a separate server which performs the physics simulation (via a communication interface 302).

When implemented in software, the collision handler 306 comprises computer executable instructions which, when executed by the processor 902, cause the processor to flag chunks involved in a collision as dirty (e.g. as in block 404).

When implemented in software, the synchronization engine 308 comprises computer executable instructions which, when executed by the processor 902, cause the processor to identify those chunks which have been flagged as dirty, classify the chunks and then select an use the corresponding synchronization scheme (e.g. as in blocks 408-418 of FIG. 4 and the corresponding blocks in FIGS. 5 and 6). The synchronization engine 308 uses data stored in the chunk state buffer 309 as described above.

The computer executable instructions may be provided using any computer-readable media that is accessible by computing based device 900. Computer-readable media may include, for example, computer storage media such as memory 908 and communications media. Computer storage media, such as memory 908, includes volatile and non-volatile, removable and non-removable media implemented in any method or technology for storage of information such as computer readable instructions, data structures, program modules or other data. Computer storage media includes, but is not limited to, RAM, ROM, EPROM, EEPROM, flash memory or other memory technology, CD-ROM, digital versatile disks (DVD) or other optical storage, magnetic cassettes, magnetic tape, magnetic disk storage or other magnetic storage devices, or any other non-transmission medium that can be used to store information for access by a computing device. In contrast, communication media may embody computer readable instructions, data structures, program modules, or other data in a modulated data signal, such as a carrier wave, or other transport mechanism. As defined herein, computer storage media does not include communication media. Therefore, a computer storage medium should not be interpreted to be a propagating signal per se. Propagated signals may be present in a computer storage media, but propagated signals per se are not examples of computer storage media. Although the computer storage media (memory 908) is shown within the computing-based device 900 it will be appreciated that the storage may be distributed or located remotely and accessed via a network or other communication link (e.g. using communication interface 302).

Although the present examples are described and illustrated herein as being implemented in one of the systems shown in FIG. 2, the system described is provided as an example and not a limitation. As those skilled in the art will appreciate, the present examples are suitable for application in a variety of different types of systems comprising any number of clients and servers and which use a hybrid synchronization model as described above.

Although the collision handler 306 is described above as being implemented in the server 202, in other examples, some or all of the collision handler functionality may be implemented on another server (e.g. server 204).

A first further example provides a server comprising: a buffer configured to store a plurality of previous states of all rigid bodies involved in a simulation, the state of a rigid body being categorized as either colliding or not colliding; a synchronization engine configured to generate synchronization packets for one or more rigid bodies according to a synchronization scheme and, for each rigid body, to dynamically update the synchronization scheme based on a current state of the rigid body in simulation data and the stored states for the rigid body; and a communication interface configured to transmit the synchronization packets to one of a plurality of client computing devices configured to perform a reduced simulation function.

The synchronization engine may be configured to dynamically update the synchronization scheme for a rigid body by detecting if the rigid body is transitioning between a continuously colliding state and steady gravitational state, in response to detecting a transition from the continuously colliding state to the steady gravitational state, updating the synchronization scheme to generate a synchronization packet comprising a full set of properties of the rigid body and in response to detecting a transition from the steady gravitational state to the continuously colliding state, updating the synchronization scheme to generate a synchronization packet to cause the simulation of the body on the client computing device to stop.

The buffer may be configured to store N previous states of a rigid body, where N is a positive integer greater than one and the synchronization engine may be configured to detect a transition from the continuously colliding state to the steady gravitational state when at least the N−1 most recent stored states for the rigid body are all not colliding, the current state is not colliding and the most recent colliding state was N or N+1 states ago and the synchronization engine is configured to detect a transition from the steady gravitational state to the continuously colliding state when at least the N−1 most recent stored states for the rigid body are all not colliding and the current state is colliding.

The full set of properties of the rigid body may comprise the rigid body's velocity, position and rotation.

The synchronization engine may be further configured to dynamically update the synchronization scheme for a rigid body by detecting if the rigid body is in the continuously colliding state or in the steady gravitational state, in response to detecting that the rigid body is in the continuously colliding state, updating the synchronization scheme to generate a synchronization packet every K collisions, each synchronization packet comprising a reduced set of properties of the rigid body and in response to detecting that the rigid body is in the steady gravitational state, updating the synchronization scheme to stop generating synchronization packets, wherein K is a positive integer.

The buffer may be configured to store N previous states of a rigid body, where N is a positive integer greater than one and the synchronization engine is configured to detect that the rigid body is in the continuously colliding state when at least the N−1 most recent stored states for the rigid body are all colliding and the current state is colliding and the synchronization engine is configured to detect that the rigid body is in the steady gravitational state when at least the N−1 most recent stored states for the rigid body are all not colliding, the current state is not colliding and the most recent colliding state more than N or N+1 states ago.

The reduced set of properties of the rigid body may comprise the rigid body's position and rotation and not the rigid body's velocity.

The synchronization engine may be further configured to dynamically adjust the value of N and/or K based, at least in part, on an available bandwidth between the server and said one of the plurality of client computing devices.

The synchronization engine may be further configured to dynamically update the synchronization scheme for a rigid body by detecting if the rigid body is in a transient state and in response to detecting that the rigid body is in the transient state, updating the synchronization scheme to stop generating synchronization packets.

The buffer may be configured to store N previous states of a rigid body, where N is a positive integer greater than one and the synchronization engine may be configured to detect that the rigid body is in the transient state when at least the N−1 most recent stored states for the rigid body are not identical.

The server may further comprise a collision handler configured to set the current state of the one or more rigid bodies as either colliding or not colliding based on a frame of the simulation data.

The server may further comprise a physics simulation engine configured to provide the simulation data, the simulation data having been generated by a simulation of both gravitational trajectories and collisions of rigid bodies.

The physics simulation engine may be further configured to perform the simulation and generate the simulation data and/or to aggregate simulation data received from other servers configured to perform the simulation.

The synchronization engine may be at least partially implemented using hardware logic selected from any one or more of: a field-programmable gate array, a program-specific integrated circuit, a program-specific standard product, a system-on-a-chip, a complex programmable logic device.

A second further example provides a server comprising: a processor; a communication interface configured to transmit synchronization packets to one of a plurality of client computing devices configured to perform a reduced simulation function; and a memory, wherein the memory is configured to store: a plurality of previous states of all rigid bodies involved in a simulation, the state of a rigid body being categorized as either colliding or not colliding; device executable instructions which, when executed by the processor, cause the processor to generate synchronization packets for one or more rigid bodies according to a synchronization scheme and, for each rigid body, to dynamically update the synchronization scheme based on a current state of the rigid body in simulation data and the stored states for the rigid body.

A third further example provides a computer implemented method comprising: storing, in a buffer and for each of a plurality of chunks involved in a simulation, a plurality of previous states of the chunk; receiving a frame of simulation data; determining, in a collision handler on a server, a current state of each chunk in the frame of simulation data as being either colliding or not colliding; updating a synchronization scheme based on the current state of the chunk and the stored states for the chunk; generating synchronization packets for one or more chunks according to the synchronization scheme for the chunks; sending the synchronization packets to one of a plurality of client computing devices configured to perform a reduced simulation function; and storing the current state of each chunk in the frame of simulation data in the buffer.

Updating a synchronization scheme based on the current state of the chunk and the stored states for the chunk may comprise: detecting if the rigid body is transitioning between a continuously colliding state and steady gravitational state; in response to detecting a transition from the continuously colliding state to the steady gravitational state, updating the synchronization scheme to generate a synchronization packet comprising a full set of properties of the rigid body; and in response to detecting a transition from the steady gravitational state to the continuously colliding state, updating the synchronization scheme to generate a synchronization packet to cause the simulation of the body on the client computing device to stop.

Updating a synchronization scheme based on the current state of the chunk and the stored states for the chunk may further comprise: detecting if the rigid body is in the continuously colliding state or in the steady gravitational state; in response to detecting that the rigid body is in the continuously colliding state, updating the synchronization scheme to generate a synchronization packet every K collisions, each synchronization packet comprising a reduced set of properties of the rigid body and wherein K is a positive integer; and in response to detecting that the rigid body is in the steady gravitational state, updating the synchronization scheme to stop generating synchronization packets.

Updating a synchronization scheme based on the current state of the chunk and the stored states for the chunk may further comprise: detecting if the rigid body is in a transient state; and in response to detecting that the rigid body is in the transient state, updating the synchronization scheme to stop generating synchronization packets.

The simulation data may be generated by a simulation of both gravitational trajectories and collisions of rigid bodies and wherein the reduced simulation function does not perform collision detection.

The term 'computer' or 'computing-based device' is used herein to refer to any device with processing capability such that it can execute instructions. Those skilled in the art will realize that such processing capabilities are incorporated into many different devices and therefore the terms 'computer' and 'computing-based device' each include PCs, servers, mobile telephones (including smart phones), tablet computers, set-top boxes, media players, games consoles, personal digital assistants and many other devices.

The methods described herein may be performed by software in machine readable form on a tangible storage medium e.g. in the form of a computer program comprising computer program code means adapted to perform all the steps of any of the methods described herein when the program is run on a computer and where the computer program may be embodied on a computer readable medium. Examples of tangible storage media include computer storage devices comprising computer-readable media such as disks, thumb drives, memory etc. and do not include propagated signals. Propagated signals may be present in a tangible storage media, but propagated signals per se are not examples of tangible storage media. The software can be suitable for execution on a parallel processor or a serial processor such that the method steps may be carried out in any suitable order, or simultaneously.

This acknowledges that software can be a valuable, separately tradable commodity. It is intended to encompass software, which runs on or controls "dumb" or standard hardware, to carry out the desired functions. It is also intended to encompass software which "describes" or defines the configuration of hardware, such as HDL (hardware description language) software, as is used for designing silicon chips, or for configuring universal programmable chips, to carry out desired functions.

Those skilled in the art will realize that storage devices utilized to store program instructions can be distributed across a network. For example, a remote computer may store an example of the process described as software. A local or terminal computer may access the remote computer and download a part or all of the software to run the program. Alternatively, the local computer may download pieces of the software as needed, or execute some software instructions at the local terminal and some at the remote computer (or computer network). Those skilled in the art will also realize that by utilizing conventional techniques known to those skilled in the art that all, or a portion of the software instructions may be carried out by a dedicated circuit, such as a DSP, programmable logic array, or the like.

Any range or device value given herein may be extended or altered without losing the effect sought, as will be apparent to the skilled person.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

It will be understood that the benefits and advantages described above may relate to one embodiment or may relate to several embodiments. The embodiments are not limited to those that solve any or all of the stated problems or those that have any or all of the stated benefits and advantages. It will further be understood that reference to 'an' item refers to one or more of those items.

The steps of the methods described herein may be carried out in any suitable order, or simultaneously where appropriate. Additionally, individual blocks may be deleted from any of the methods without departing from the spirit and scope of the subject matter described herein. Aspects of any of the examples described above may be combined with aspects of any of the other examples described to form further examples without losing the effect sought.

The term 'comprising' is used herein to mean including the method blocks or elements identified, but that such blocks or elements do not comprise an exclusive list and a method or apparatus may contain additional blocks or elements.

It will be understood that the above description is given by way of example only and that various modifications may be made by those skilled in the art. The above specification, examples and data provide a complete description of the structure and use of exemplary embodiments. Although various embodiments have been described above with a certain degree of particularity, or with reference to one or more individual embodiments, those skilled in the art could make numerous alterations to the disclosed embodiments without departing from the spirit or scope of this specification.

The invention claimed is:

1. A server comprising:
   a buffer configured to store a plurality of previous states of all rigid bodies involved in a simulation, the state of a rigid body being categorized as either colliding or not colliding;
   a synchronization engine configured to generate synchronization packets for one or more rigid bodies according to a synchronization scheme and, for each rigid body, to dynamically update the synchronization scheme based on a current state of the rigid body in simulation data and the stored states for the rigid body; and
   a communication interface configured to transmit the synchronization packets to one of a plurality of client computing devices configured to perform a reduced simulation function.

2. A server according to claim 1, wherein the synchronization engine is configured to dynamically update the synchronization scheme for a rigid body by detecting if the rigid body is transitioning between a continuously colliding state and steady gravitational state, in response to detecting a transition from the continuously colliding state to the steady gravitational state, updating the synchronization scheme to generate a synchronization packet comprising a full set of properties of the rigid body and in response to detecting a transition from the steady gravitational state to the continuously colliding state, updating the synchronization scheme to generate a synchronization packet to cause the simulation of the body on the client computing device to stop.

3. A server according to claim 2, wherein the buffer is configured to store N previous states of a rigid body, where N is a positive integer greater than one and the synchronization engine is configured to detect a transition from the continuously colliding state to the steady gravitational state when at least the N−1 most recent stored states for the rigid body are all not colliding, the current state is not colliding and the most recent colliding state was N or N+1 states ago and the synchronization engine is configured to detect a transition from the steady gravitational state to the continuously colliding state when at least the N−1 most recent stored states for the rigid body are all not colliding and the current state is colliding.

4. A server according to claim 2, wherein the full set of properties of the rigid body comprises the rigid body's velocity, position and rotation.

5. A server according to claim 2, wherein the synchronization engine is further configured to dynamically update the synchronization scheme for a rigid body by detecting if the rigid body is in the continuously colliding state or in the steady gravitational state, in response to detecting that the rigid body is in the continuously colliding state, updating the synchronization scheme to generate a synchronization packet every K collisions, each synchronization packet comprising a reduced set of properties of the rigid body and in response to detecting that the rigid body is in the steady gravitational state, updating the synchronization scheme to stop generating synchronization packets, wherein K is a positive integer.

6. A server according to claim 5, wherein the buffer is configured to store N previous states of a rigid body, where N is a positive integer greater than one and the synchronization engine is configured to detect that the rigid body is in the continuously colliding state when at least the N−1 most recent stored states for the rigid body are all colliding and the current state is colliding and the synchronization engine is configured to detect that the rigid body is in the steady gravitational state when at least the N−1 most recent stored states for the rigid body are all not colliding, the current state is not colliding and the most recent colliding state more than N or N+1 states ago.

7. A server according to claim 5, wherein the reduced set of properties of the rigid body comprises the rigid body's position and rotation and does not comprise the rigid body's velocity.

8. A server according to claim 5, wherein the synchronization engine is further configured to dynamically adjust the value of N and/or K based, at least in part, on an available bandwidth between the server and said one of the plurality of client computing devices.

9. A server according to claim 5, wherein the synchronization engine is further configured to dynamically update the synchronization scheme for a rigid body by detecting if the rigid body is in a transient state and in response to detecting that the rigid body is in the transient state, updating the synchronization scheme to stop generating synchronization packets.

10. A server according to claim 9, wherein the buffer is configured to store N previous states of a rigid body, where N is a positive integer greater than one and the synchronization engine is configured to detect that the rigid body is in the transient state when at least the N−1 most recent stored states for the rigid body are not identical.

11. A server according to claim 1, further comprising:
a collision handler configured to set the current state of the one or more rigid bodies as either colliding or not colliding based on a frame of the simulation data.

12. A server according to claim 1, further comprising:
a physics simulation engine configured to provide the simulation data, the simulation data having been generated by a simulation of both gravitational trajectories and collisions of rigid bodies.

13. A server according to claim 12, wherein the physics simulation engine is further configured to perform the simulation and generate the simulation data and/or to aggregate simulation data received from other servers configured to perform the simulation.

14. A server according to claim 1, the synchronization engine being at least partially implemented using hardware logic selected from any one or more of: a field-programmable gate array, a program-specific integrated circuit, a program-specific standard product, a system-on-a-chip, a complex programmable logic device.

15. A server comprising:
a processor;
a communication interface configured to transmit synchronization packets to one of a plurality of client computing devices configured to perform a reduced simulation function; and
a memory, wherein the memory is configured to store:
a plurality of previous states of all rigid bodies involved in a simulation, the state of a rigid body being categorized as either colliding or not colliding;
device executable instructions which, when executed by the processor, cause the processor to generate synchronization packets for one or more rigid bodies according to a synchronization scheme and, for each rigid body, to dynamically update the synchronization scheme based on a current state of the rigid body in simulation data and the stored states for the rigid body.

16. A computer implemented method comprising:
storing, in a buffer and for each of a plurality of chunks involved in a simulation, a plurality of previous states of the chunk;
receiving a frame of simulation data;
determining, in a collision handler on a server, a current state of each chunk in the frame of simulation data as being either colliding or not colliding;
updating a synchronization scheme based on the current state of the chunk and the stored states for the chunk;
generating synchronization packets for one or more chunks according to the synchronization scheme for the chunks;
sending the synchronization packets to one of a plurality of client computing devices configured to perform a reduced simulation function; and
storing the current state of each chunk in the frame of simulation data in the buffer.

17. A computer implemented method according to claim 16, wherein updating a synchronization scheme based on the current state of the chunk and the stored states for the chunk comprises:
detecting if the rigid body is transitioning between a continuously colliding state and steady gravitational state;
in response to detecting a transition from the continuously colliding state to the steady gravitational state, updating the synchronization scheme to generate a synchronization packet comprising a full set of properties of the rigid body; and
in response to detecting a transition from the steady gravitational state to the continuously colliding state, updating the synchronization scheme to generate a synchronization packet to cause the simulation of the body on the client computing device to stop.

18. A computer implemented method according to claim 17, wherein updating a synchronization scheme based on the current state of the chunk and the stored states for the chunk further comprises:
- detecting if the rigid body is in the continuously colliding state or in the steady gravitational state;
- in response to detecting that the rigid body is in the continuously colliding state, updating the synchronization scheme to generate a synchronization packet every K collisions, each synchronization packet comprising a reduced set of properties of the rigid body and wherein K is a positive integer; and
- in response to detecting that the rigid body is in the steady gravitational state, updating the synchronization scheme to stop generating synchronization packets.

19. A computer implemented method according to claim 18, wherein updating a synchronization scheme based on the current state of the chunk and the stored states for the chunk further comprises:
- detecting if the rigid body is in a transient state; and
- in response to detecting that the rigid body is in the transient state, updating the synchronization scheme to stop generating synchronization packets.

20. A computer implemented method according to claim 16, wherein the simulation data is generated by a simulation of both gravitational trajectories and collisions of rigid bodies and wherein the reduced simulation function does not perform collision detection.

* * * * *